United States Patent
Barker et al.

(10) Patent No.: US 10,000,843 B2
(45) Date of Patent: Jun. 19, 2018

(54) COATING PROCESS FOR NON-CONDUCTIVE SUBSTRATES AND DEVICES MADE FROM THE COATING PROCESS

(71) Applicant: DePuy Synthes Products, LLC, Raynham, MA (US)

(72) Inventors: Paul Barker, Wallisellen (CH); Jörg Patscheider, Meilen (CH); Götz Thorwarth, Oberdorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 790 days.

(21) Appl. No.: 14/479,926

(22) Filed: Sep. 8, 2014

(65) Prior Publication Data

US 2015/0075995 A1    Mar. 19, 2015

Related U.S. Application Data

(60) Provisional application No. 61/877,534, filed on Sep. 13, 2013.

(51) Int. Cl.
    *C23C 14/00* (2006.01)
    *C23C 14/35* (2006.01)
    (Continued)

(52) U.S. Cl.
    CPC .......... *C23C 14/35* (2013.01); *A61B 17/80* (2013.01); *A61B 17/84* (2013.01); *A61F 2/44* (2013.01);
    (Continued)

(58) Field of Classification Search
    CPC ........ C23C 14/35; C23C 14/20; C23C 14/205
    See application file for complete search history.

(56) References Cited

U.S. PATENT DOCUMENTS

5,015,493 A * 5/1991 Gruen ............... C23C 14/32
                                                 204/298.05
6,121,172 A * 9/2000 Marcolongo ......... A61F 2/367
                                                 424/76.8
(Continued)

FOREIGN PATENT DOCUMENTS

EP        1923079      5/2008
WO    2015038489      3/2015

OTHER PUBLICATIONS

Rabiei, Afsaneh, Stefan Sandukas, Processing and evaluation of bioactive coatings on polymeric implants. J Biomed Mater Res Part A, Feb. 15, 2013: 101A: 2621-2629.*

(Continued)

*Primary Examiner* — John J Brayton
(74) *Attorney, Agent, or Firm* — Morgan, Lewis & Bockius LLP

(57) ABSTRACT

A method for manufacturing a surgical implant. A metal layer is deposited onto a polyaryletherketone (PAEK) substrate by generating a series of pulses using a high power impulse magnetron sputtering process. Each pulse is applied in a series of micro pulse steps comprising (i) micro pulse on steps ranging from 10 μs to 100 μs and (ii) micro pulse off steps ranging from 5 μs as to 400 μs; at a repetition frequency ranging from 50-2000 Hz with 2 micropulses to 20 micropulses per repetition, a total pulse on time ranging from 25 μs to 800 μs for 5 minutes to 300 minutes at averaged power ranging from 200 W to 3000 W. The series of pulses are performed in a unipolar mode or a bipolar mode.

17 Claims, 2 Drawing Sheets

(51) Int. Cl.
  A61B 17/80    (2006.01)
  A61B 17/84    (2006.01)
  A61F 2/44     (2006.01)
  C23C 14/34    (2006.01)
  C23C 28/00    (2006.01)
  A61L 27/18    (2006.01)
  A61L 27/30    (2006.01)
  A61L 31/06    (2006.01)
  A61L 31/08    (2006.01)

(52) U.S. Cl.
  CPC .............. *A61L 27/18* (2013.01); *A61L 27/306* (2013.01); *A61L 31/06* (2013.01); *A61L 31/088* (2013.01); *C23C 14/3485* (2013.01); *C23C 28/00* (2013.01); *A61F 2310/00407* (2013.01); *A61F 2310/00544* (2013.01); *A61L 2420/02* (2013.01); *A61L 2430/02* (2013.01); *A61L 2430/24* (2013.01); *A61L 2430/38* (2013.01)

(56) References Cited

U.S. PATENT DOCUMENTS

2008/0135400 A1* 6/2008 Kadlec ................. H01J 37/3444
                                                    204/192.12
2009/0057133 A1* 3/2009 Kouznetsov ........ C23C 14/0068
                                                    204/192.12
2012/0310368 A1* 12/2012 Voisard ................. A61L 27/306
                                                    623/23.76

OTHER PUBLICATIONS

Han, Cheol-Min, et al., The electron beam deposition of titanium on polyetheretherketone (PEEK) and the resulting enhanced biological properties. Biomaterials 31 (2010) 3465-3470.*

Arutiun P. Ehiasarian, "High-power impulse magnetron sputtering and its applications", Pure and Applied Chemistry, vol. 82, No. 6, Jan. 20, 2010, pp. 1248-1258.

Krause U. et al., "Requirements of power supply parameters for high-power pulsed magnetron sputtering", Thin Solid Films, Elsevier-Sequoia S.A. Lausanne, CH, vo. 392, No. 2, Jul. 30, 2001, pp. 196-200.

Konstantinidis S. et al., "Deposition of zinc oxide layers by high-power impulse magnetron sputtering", Journal of Vacuum Science and Technology: Part B, Avs/Aip, Melville, NY, vol. 25, No. 3, May 8, 2007, pp. 19-21.

The International Search Report for International Patent Application No. PCT/US2014/054650, dated Nov. 24, 2014, 6 pages.

The Written Opinion for International Patent Application No. PCT/US2014/054650, dated Nov. 24, 2014, 4 pages.

* cited by examiner

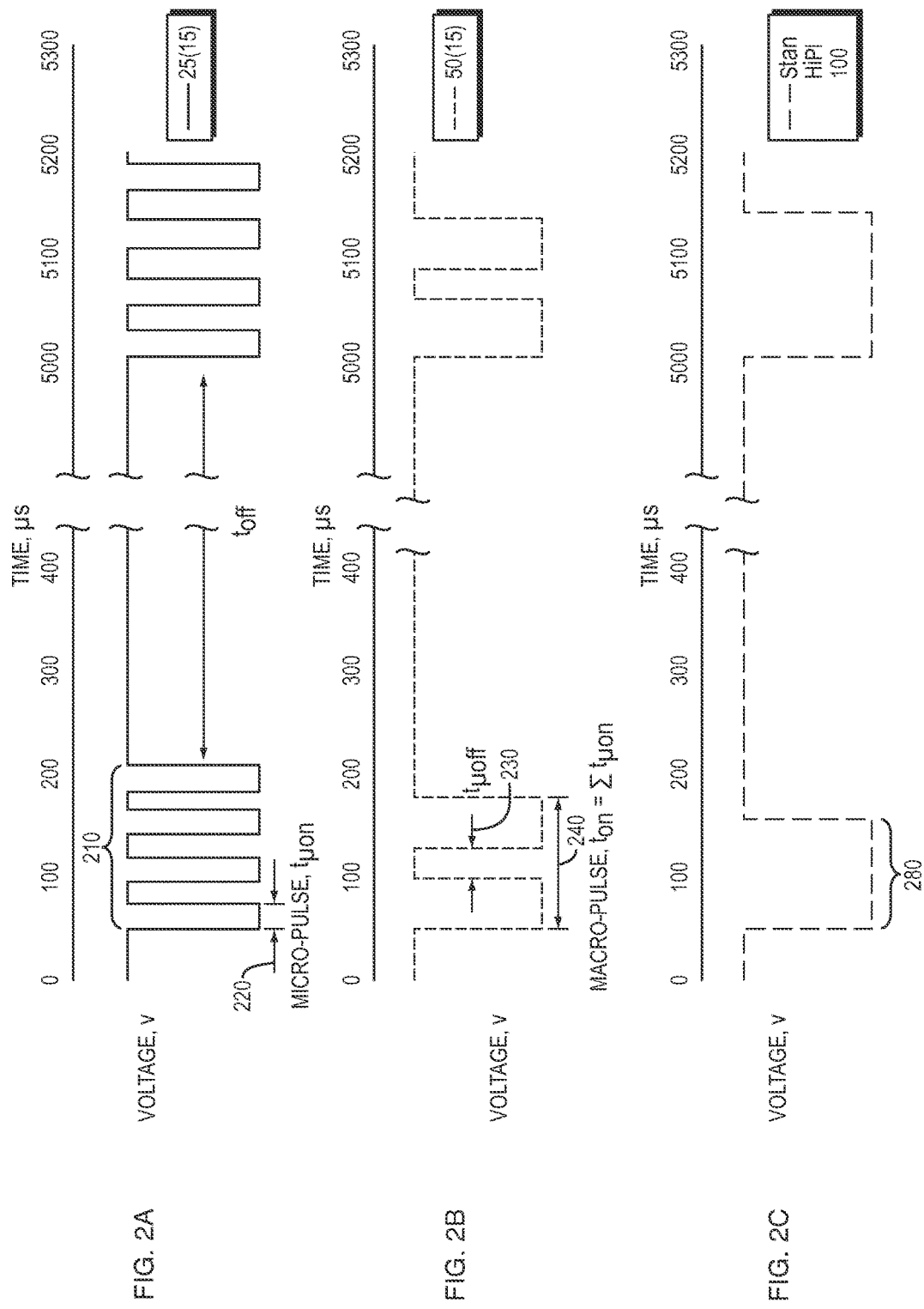

COATING PROCESS FOR NON-CONDUCTIVE SUBSTRATES AND DEVICES MADE FROM THE COATING PROCESS

CROSS-REFERENCE TO RELATED APPLICATIONS

The present application claims priority to U.S. Provisional Application No. 61/877,534 filed Sep. 13, 2013, the entire contents of which is incorporated herein by reference in its entirety.

FIELD OF THE INVENTION

The present invention relates to a coating process using a new process based on high power impulse magnetron sputtering and medical devices made using this process.

BACKGROUND OF THE INVENTION

PEEK and related plastics are preferred materials for implants since they excel over conventional plastics due to their mechanical durability. For many implant applications however, a drawback lies in the poor biological integration of these materials' surface. Therefore, a biocompatible coating is an obvious solution with the requirements of strong adhesion, chemical stability, and conformity to the implant surface; the latter is especially important for spinal spacer devices to maintain primary stability.

High power impulse magnetron sputtering ("HiPIMS"), also known as HPPMS, as a novel deposition technology has been published in 1999 by Kousnetzov et al (V. Kouznetsov, K. Macak, J. M. Schneider, U. Helmersson, I. Petrov, Surf. Coat. Technol. Volume 122, Issue 2-3 (1999) 290-293). This technique attracted considerable attention in the last ten years, and a large scientific community evolved utilizing this technology, while the few industrial applications are mainly focusing on wear-protective coatings.

The present disclosure describes novel modifications to the HiPIMS process and medical devices resulting from such novel process.

SUMMARY OF THE INVENTION

In one aspect, the present disclosure provides for a method for manufacturing a surgical implant. A metal layer is deposited onto a polyaryletherketone substrate by generating a series of bipolar pulses using a high power impulse magnetron sputtering process wherein the bipolar pulses are applied at a repetition frequency ranging from 50 Hz to 2000 Hz, a total pulse on time ranging from 25 µs to 800 µs as for 5 minutes to 300 minutes at averaged power ranging from 200 W to 3000 W.

In another one aspect, the present disclosure further provides for a method for manufacturing a surgical implant. A metal layer is deposited onto a polyaryletherketone (PAEK) substrate by generating a series of pulses using a high power impulse magnetron sputtering process. Each pulse is applied in a series of micro pulse steps comprising (i) micro pulse on steps ranging from 10 µs to 100 µs and (ii) micro pulse off steps ranging from 5 µs to 400 µs; at a repetition frequency ranging from 50-2000 Hz with 2 micropulses to 20 micropulses per repetition, a total pulse on time ranging from 25 µs to 800 µs for 5 minutes to 300 minutes at averaged power ranging from 200 W to 3000 W. In one embodiment, the series of pulses are performed in a unipolar mode. In another embodiment, the series of pulses are performed in a bipolar mode.

In one embodiment, the methods described herein further include the steps of: immersing the surgical implant into simulated body fluid (SBF) for a time period to thereby form a calcium phosphate layer.

In another embodiment, the methods described herein further include the step of converting the metal layer using an anodization process performed in an acidic solution to thereby form a nano-porous exterior surface.

In yet another embodiment, the methods described herein further include the step of: converting the metal layer using an anodization process with an electrolyte containing Ca and P ions to thereby form a microporous layer containing Ca and P ions.

In another aspect, the present disclosure provides for a surgical implant including a polyaryletherketone (PAEK) substrate having an exterior surface and at least one metal layer disposed over the substrate exterior surface wherein the static axial adhesion strength between the substrate and the metal layer is at least 28 MPa. In one embodiment, the static axial adhesion strength between the substrate and the metal layer ranges from 28 MPa to 50 MPa.

For the various embodiments described herein, the polyaryletherketone (PAEK) is independently selected from polyetherketone (PEK), fiber reinforced PEK, polyetheretherketone (PEEK), fiber reinforced PEEK, polyetherketoneketone (PEKK), fiber reinforced PEKK, polyetheretherketoneketone (PEEKK), fiber reinforced PEEKK, polyetherketoneetherketoneketone (PEKEKK) and fiber reinforced PEKEKK.

For the various embodiments described herein, the metal layer is independently selected from Al, Cr, Zr, Nb, Rh, Pd, Ag, W, Pt, Au, Ta or Ti.

For the various embodiments described herein, the surgical implant includes cages and spacers; bone anchors; cranial meshes and articulations.

BRIEF DESCRIPTION OF THE SEVERAL VIEWS OF THE DRAWINGS

The foregoing summary, as well as the following detailed description of embodiments of the surgical implant of the present invention, will be better understood when read in conjunction with the appended drawings of exemplary embodiments. It should be understood, however, that the invention is not limited to the precise arrangements and instrumentalities shown. In the drawings:

FIGS. 2A-2C illustrate a bipolar HiPIMS and bipolar chopped HiPMS sequence according an embodiment of the present disclosure compared to a prior art process.

DETAILED DESCRIPTION OF THE EMBODIMENTS

Figure 1A:
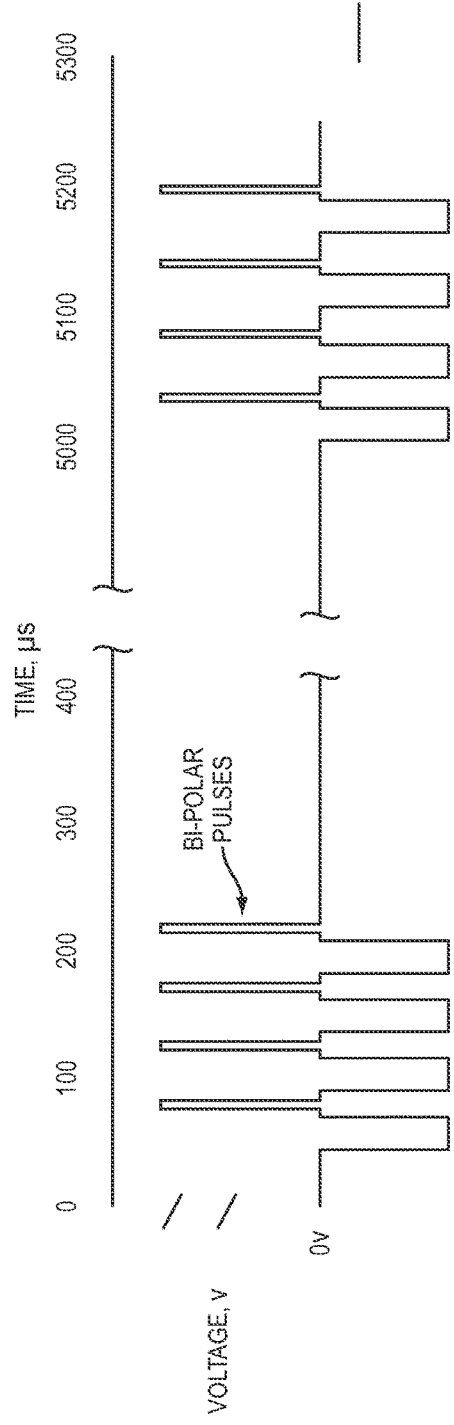
FIGS. 1A and 1B illustrate an exemplary method of a bipolar HiPIMS pulse sequence.

The present subject matter will now be described more fully hereinafter with reference to the accompanying figures and examples, in which representative embodiments are shown. The present subject matter can, however, be embodied in different forms and should not be construed as limited to the embodiments or examples set forth herein.

The present disclosure provides for a new coating process based on HiPIMS that improves upon the basic technique to give improved adhesion and layer quality of a metal disposed onto a polyaryletherketone substrate. It does so by providing excited species at high concentrations during the process that provides excellent adhesion and dense coatings. While standard sputter deposition techniques yield coatings with insufficient adhesion, we have observed that unipolar HiPIMS and even more so bipolar HiPIMS produce metal coatings with improved adhesion. Moreover, we have found that chopped HiPIMS ("c-HiPIMS") allows tuning various properties of the deposition plasma and hence of the deposited coating itself. This technique may be applied both in unipolar and in bipolar HiPIMS.

In one aspect, the present disclosure provides for a method for manufacturing a surgical implant. A metal layer is deposited onto a polyaryletherketone substrate by generating a series of bipolar pulses using a high power impulse magnetron sputtering process. In one embodiment, the series of bipolar pulses are applied at a repetition frequency of 50 Hz to 2000 Hz, total pulse on time of 25 μs to 800 μs for 5 minutes to 300 minutes at time averaged power of 200 W to 3000 W. In another embodiment, the series of bipolar pulses are applied at a repetition frequency of 150 Hz to 400 Hz, total pulse on of 50 μs to 400 μs, for 40 minutes to 120 minutes at time averaged power of 1000 W-3000 W time.

In another one aspect, the present disclosure further provides for a method for manufacturing a surgical implant. A metal layer is deposited onto a polyaryletherketone (PAEK) substrate by generating a series of pulses using a high power impulse magnetron sputtering process. In one embodiment, each pulse is applied in a series of micro pulse steps comprising (i) micro pulse on steps ranging from 10 μs to 100 μs and (ii) micro pulse off steps ranging from 5 μs to 400 μs; at a repetition frequency ranging from 50 Hz to 2000 Hz with 2 micropulses to 20 micropulses per repetition, a total pulse on time ranging from 25 μs to 800 μs for 5 minutes to 300 minutes at time averaged power ranging from 200 W to 3000 W. In another embodiment, each pulse is applied in a series of micro pulse steps comprising (i) micro pulse on steps ranging from 25 μs to 50 μs (ii) micro pulse off steps ranging from 40 μs to 200 μs; at a repetition frequency ranging from 150 Hz to 400 Hz, with 4 micropulses to 10 micropulses per repetition, a total pulse on time ranging from 40 minutes to 120 minutes at time averaged power ranging from 1000 W to 3000 W. In certain embodiment, the series of pulses are performed in a unipolar mode. In another embodiment, the series of pulses are performed in a bipolar mode.

Figure 1B:
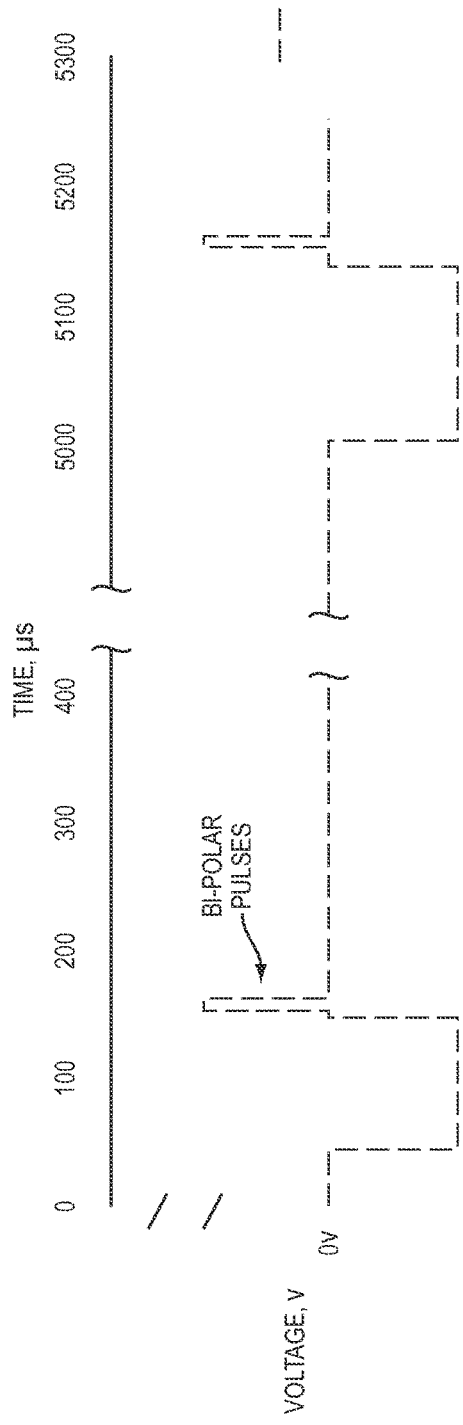

FIGS. 1A and 1B illustrate an exemplary method of bipolar HiPIMS pulse sequence, respectively. In FIG. 1A, the series of four bipolar pulses are generated using HiPiMS at a repetition frequency of 200 Hz, micro pulse on step of 25 μs, micro pulse off step of 15 μs for four micropulses, 110. FIG. 1B illustrates a prior art biopolar HiPIMS pulse sequence where a single pulse is applied at a repetition frequency of 200 Hz, and a pulse time on of 120 μs.

FIGS. 2A-2B illustrate an exemplary method compared to a prior art HiPIMS pulse sequence illustrated in FIG. 2C. In FIG. 2A, the series of four micro pulse steps, 210 are generated using c-HiPiMS at a repetition frequency of 200 Hz, micro pulse step on of 25 μs, and micro pulse step off of 15 μs. In FIG. 2B, the series of two micro pulse steps, 240, are generated using c-HiPiMS at a repetition frequency of 200 Hz, micro pulse step on of 50 μs, micro pulse step off of 15 μs. In FIG. 2C, a single micro pulse, 280 is generated using HiPiMS at a repetition frequency of 200 Hz.

In such embodiments of c-HiPIMS, the pulse is chopped into a sequence of short single micro pulses each separated by off-times. It was observed that as pulse time increases, currents can increase which can increase the ion-to-atom ratio (leading to higher ion bombardment of the growing film and therefore improved film structures) and the ion energy. However, when the pulse times increase further to about 40 μs significant heating of the working gas, argon, was observed and thus a reduction of the argon density in the near cathode region (rarefaction). Magnetron sputtering occurs through either sustained self sputtering, ("SSS"), or argon bombardment. As the gas density reduces, SSS becomes the significant sputter mechanism. However, SSS has a much reduced sputter rate compared to argon bombardment, leading to reduced deposition rates.

It was unexpectedly found that the use of shorter pulse-on times, micropulses, (where the total pulse on time is the same during a repetition frequency) avoids the onset of significant self-sputtering, known to reduce deposition rate, as well as reduced gas rarefaction. It was also discovered that c-HiPIMS allows the use of shorter pulse-on times whilst allowing higher peak currents and deposition rates, which may otherwise be reduced using short pulse-on times with HiPIMS. While not being bound to theory, it is believed that c-HiPIMS micro-pulse-off times allow for a relaxation of ion retention in the near cathode region and also resulting in increased deposition rates. Further it is believed that, these short pulse-off times allow opportunities for adatom arrangement on the substrate surface without further flux bombardment, leading to more organized and denser films.

In embodiments described herein, c-HiPIMS can be used in either unipolar or bipolar mode. As used herein, unipolar means having the sputter target switched as the cathode. As used herein, bipolar means for a first period of time the target is switched as the cathode and then switched off for a time off period, followed by a second period of time where the target is switched as the anode, where the second period of time is the less than the first period of time. The first time period, time off period and the second time period may be about 8 μs to 300 μs. The counter electrode to the target may be the chamber wall and/or the sample. Because HiPIMS is clearly distinct from RF discharges, the discharge physics at the cathode and anode are different. It may therefore not be confused with RF discharges.

In the embodiments described herein, the pulses or micropulses may be applied at a repetition frequency ranging from 50 Hz to 2000 Hz. As used herein, repetition frequency describes how often a discharge pulse is repeated. It has been observed that repetition frequency determines the properties of the deposited coatings. In some embodiments, it has been observed that repetition frequencies of up to 2000 Hz, while keeping the total time on constant, result in higher deposition rates. In such embodiments, the repetition frequencies may also vary between 500 Hz to 2000 Hz. In such other embodiments, it has been observed that at such repetition frequencies, while maintaining time averaged power constant, results in decreased average power per pulse leading to lower ion-to-atom ratios and lower ion energies which results in porous, less dense films. It is believed that such repetition frequencies may be an advantage when open pore structures are needed, e.g. for reducing stress in the grown films, to generate large internal surface areas for reactions such as anodization and the like.

In other embodiments, it has been observed that repetition frequencies down to 50 Hz produces films at lower deposition rates but with at a high ion to-atom ratio resulting in films that are have a glassy microstructure with often enhanced properties such as conductivity, hardness, etc.

In the embodiments described herein, the averaged power ranges from 200 W to 3000 W. It was found that varying the average power changes the energy supplied during the pulse on time. It was found that increase the average power, the arriving flux at the substrate has higher energy and may lead to more dense films although stress may also increase. It was also found that increasing the voltage at the cathode results in increased deposition rates.

For the embodiments described herein, the processes may be performed using a noble gas, He, Ne, Ar, Kr, Xe, for use as a working gas. In one embodiment, the processes are performed using Ar as the working gas.

For the embodiments described herein, the processes may be performed at pressure range within the range of 0.1 and 10 Pa. Below 0.1 Pa it is difficult to establish a plasma, whilst above 10 Pa there is significant scattering of the sputtered flux resulting in low deposition rates.

For the embodiments described herein, the processes may be performed at varying pulse height, which is actual the potential difference (in units of Volt) applied to the target with respect to ground potential, and is set in view of the other process parameters, i.e., repetition frequency, pulse time, etc.

In one embodiment, the methods described herein further include immersing the surgical implant into simulated body fluid (SBF) for a time period to thereby form a hydroxyapatite layer. In such embodiments, the surgical implant is immersed in SBF at a temperature of about 65° C. for a time period of 1 hour to 1 week, with a preferred time period of 24 hours.

In another embodiment, the methods described herein further include the step of: converting the metal layer using an anodization process performed in an acidic solution to thereby form a nano-porous exterior surface. In such embodiments, the acidic solution may be sulfuric acid or phosphoric acid, at a concentration ranging from 0.1 vol. %, to 90 vol. %, for 1 second to 1 minute at a DC voltage of 0 V to 300 V, preferably 5 V to 150 V.

In yet another embodiment, the methods described herein further include the step of: converting the metal layer using an anodization process with an electrolyte containing Ca and P ions to thereby form a microporous layer containing Ca and P ions. In some such embodiments, electrolyte and molar concentration may be independently chosen from $Ca(H_2PO_4)_2$ at 0.025 M, $Ca(OH)_2$ at 0.075 M, $EDTA.Na_2$ at 0.12 M, NaOH at 0.175 M and a voltage ranging from 150 V to 300 V and time ranging from 1 second to 3600 seconds, preferred 10 seconds to 180 seconds.

In another aspect, the present disclosure provides for a surgical implant which may be formed by the various embodiments described herein.

In one embodiment, the surgical implant includes a polyaryletherketone (PAEK) substrate having an exterior surface and at least one metal layer disposed over the substrate exterior surface wherein the static axial adhesion strength between the substrate and the metal layer is at least 28 MPa. In one embodiment, the static axial adhesion strength between the substrate and the metal layer ranges from 28 MPa to 50 MPa.

For the various embodiments described herein, the polyaryletherketone (PAEK) is independently selected from polyetherketone (PEK), fiber reinforced PEK, polyetheretherketone (PEEK), fiber reinforced PEEK, polyetherketoneketone (PEKK), fiber reinforced PEKK, polyetheretherketoneketone (PEEKK), fiber reinforced PEEKK, polyetherketoneetherketoneketone (PEKEKK) and fiber reinforced PEKEKK. In one embodiment, the polyaryletherketone (PAEK) is polyetheretherketone (PEEK). In another embodiment, the polyaryletherketone (PAEK) is polyetherketoneketone (PEKK). In yet another embodiment, the pol-yaryletherketone (PAEK) is fiber reinforced polyetheretherketone (PEEK). In still yet another embedment, the polyaryletherketone (PAEK) is fiber reinforced polyetherketoneketone (PEKK).

For the various embodiments described herein, the metal layer is independently selected from: Al, Cr, Zr, Nb, Rh, Pd, Ag, W, Pt, Au, Ta or Ti. In some embodiments, the metal layer is independent selected from Ti or Ta. In another embodiment, the metal layer is Ta. In still yet another embodiment, the metal layer is Ti. In certain embodiments, the layer thickness is at least 200 nm.

For the various embodiments described herein, the surgical implant includes cages and spacers; bone anchors; cranial meshes and articulations.

EXAMPLES

Example 1

A vertebral spacer for the lumbar spine made from a PEEK substrate was coated with a 200 nm tantalum/titanium layer using the following process. The PEEK substrate was ultrasonically cleaned in ethanol for 5 minutes and then inserted into a vacuum system followed by plasma activation in RF oxygen plasma, ion density $1e^{10}$ cm$^{-3}$, for 5 minutes. The substrate was then coated with Ta using a c-HIPIMS pulse sequence of: repetition frequency 100 Hz; micro pulse-on time 100 microseconds; micro pulse off-time 20 microseconds; averaged power 1 kW; and process duration 1 hour. A SIPP2000 HiPIMS pulser from Melee GmbH (Baden-Baden, Germany) was used powered by an "Advanced Energy Pinnacle" power supply (Advanced Energy, Fort Collins, USA). The coated substrate was removal from vacuum chamber followed by anodization treatment in phosphoric acid.

Example 2

A bone anchor made from a PEEK substrate was coated with a 20 nm titanium layer in the following process. The PEEK substrate was ultrasonically cleaned in isopropyl alcohol for 10 minutes then inserted into a vacuum plasma cleaner followed by plasma activation in a microwave argon/oxygen plasma for 3 minutes. The substrate was then coated with Ti using a c-HIPIMS pulse sequence of: repetition frequency 2000 Hz; micro pulse-on time 30 microseconds; micro pulse off-time 5 microseconds; averaged power 3000 W; process duration 15 minutes. A HiPIMS pulser, as described in Example 1, was used.

Example 3

An osteosynthesis plate for cranial flap fixation was made from PAEK substrate coated with a 50 nm zirconium layer using the following process. The substrate was ultrasonically cleaned in ethanol for 10 minutes followed by plasma activation in a $H_2O$ RF plasma for 5 minutes. The substrate was then coated with Zr using a c-HIPIMS pulse sequence of: repetition frequency 500 Hz; micro pulse on-time 500 microseconds; micro pulse-off time 50 microseconds; averaged power 1000; process duration 200 minutes.

Example 4

A series of Ti coated PEEK substrates were prepared with using a unipolar HiPIMS pulse series. The macro-pulse consisted of micro-pulses of 25 µs, followed by a micro-off period of 100 µs. This sequence is iterated 8 times, to form the macro-pulse. This was repeated at a frequency of 200 Hz, at a time averaged power of 1 kW. The adhesion strength of each coated substrate was measured using the parameters described in ASTM F 1147. The adhesion strength was 35.0 MPa with a standard deviation of 3.5 MPa.

Example 5

A series of Ti coated PEEK substrates were prepared with using a bipolar HiPIMS pulse series. The macro-pulse consisted of micro-pulses of 25 µs, followed by an micro-off period of 5 µs, a reverse (positive) voltage pulse of 10 µs and a further micro-off period of 100 µs. This sequence is iterated 8 times, to form the macro-pulse. This was repeated at a frequency of 200 Hz, at a time averaged power of 1 kW. The adhesion strength of each coated substrate was measured using the parameters described in ASTM F 1147. The adhesion strength was 38.2 MPa with a standard deviation of 2.7 MPa.

Comparative Example

A series of Ti coated PEEK substrates were prepared using Arc evaporation. The adhesion strength of each coated substrate was measured using the parameters described in ASTM F 1147. The average adhesion strength was 23.8 MPa.

A series of Ti coated PEEK substrates were prepared using magnetron sputtering. The adhesion strength of each coated substrate was measured using the parameters described in ASTM F 1147. The average adhesion strength was 25 MPa.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It should be understood that various changes, substitutions, and alterations can be made herein without departing from the spirit and scope of the invention as defined by the appended claims. It should also be apparent that individual elements identified herein as belonging to a particular embodiment may be included in other embodiments of the invention. Moreover, the scope of the present application is not intended to be limited to the particular embodiments of the process, machine, manufacture, and composition of matter, means, methods and steps described in the specification. As one of ordinary skill in the art will readily appreciate from the disclosure herein, processes, machines, manufacture, composition of matter, means, methods, or steps, presently existing or later to be developed that perform substantially the same function or achieve substantially the same result as the corresponding embodiments described herein may be utilized according to the present invention. Furthermore, all publications, patent applications, patents, and other references mentioned herein are explicitly incorporated by reference in their entirety.

What is claimed:

1. A method for manufacturing a surgical implant comprising the steps of:
   depositing a metal layer onto a polyaryletherketone substrate by generating a series of bipolar pulses using a magnetron sputtering process, wherein the bipolar pulses are applied at a repetition frequency ranging from 50 Hz to 2000 Hz for 5 minutes to 300 minutes at averaged power ranging from 200 W to 3000 W, wherein each bipolar pulse includes a series of micro pulse on steps and micro pulse off steps, a total time of the micro pulse on steps for each bipolar pulse ranging from 25 µs to 800 µs, and
   wherein an adhesion strength between the polyaryletherketone substrate and the metal layer ranges from 28 MPa to 50 MPa.

2. A method for manufacturing a surgical implant comprising the steps of:
   depositing a metal layer onto a polyaryletherketone (PAEK) substrate by generating a series of pulses using a magnetron sputtering process, wherein each pulse is applied in a series of micro pulse steps comprising (i) micro pulse on steps ranging from 10 µs to 100 µs and (ii) micro pulse off steps ranging from 5 µs to 400 µs; at a repetition frequency ranging from 50-2000 Hz with 2 micropulses to 20 micropulses per repetition for 5 minutes to 300 minutes at averaged power ranging from 200 W to 3000 W, wherein a total time of the micro pulse on steps for each pulse ranging from 25 µs to 800 µs, and
   wherein an adhesion strength between the polyaryletherketone substrate and the metal layer ranges from 28 MPa to 50 MPa.

3. The method according to claim 2, wherein the series of pulses are performed in a unipolar mode.

4. The method according to claim 2, wherein the series of pulses are performed in a bipolar mode.

5. The method according to any of claims 1 and 2, wherein the polyaryletherketone (PAEK) is independently selected from a group consisting of polyetherketone (PEK), fiber reinforced PEK, polyetheretherketone (PEEK), fiber reinforced PEEK, polyetherketoneketone (PEKK), fiber reinforced PEKK, polyetheretherketoneketone (PEEKK), fiber reinforced PEEKK, polyetherketoneetherketoneketone (PEKEKK) and fiber reinforced PEKEKK.

6. The method according to claim 5, wherein the metal layer is independently selected from the group consisting of: Al, Cr, Zr, Nb, Rh, Pd, Ag, W, Pt, Au, Ta or Ti.

7. The method according to claim 6, wherein the metal layer is independently selected from the group consisting of: Ta or Ti.

8. The method according to claim 7, wherein the metal layer is Ti.

9. The method according to any of claims 1 and 2, wherein the depositing step is conducted in an oxygen atmosphere.

10. The method according to claim 7, further comprising the steps of:
    immersing the surgical implant into simulated body fluid (SBF) for a second time period to thereby form a calcium phosphate layer.

11. The method according to claim 7, further comprising the step of: converting the metal layer using an anodization process performed in an acidic solution to thereby form a nano-porous exterior surface.

12. The method according to claim 7, further comprising the step of: converting the metal layer using an anodization process with an electrolyte containing Ca and P ions to thereby form a microporous layer containing Ca and P ions.

13. The method according to claim 1, wherein the series of bipolar pulses are applied at a repetition frequency of 150 Hz to 400 Hz for 40 minutes to 120 minutes.

14. The method according to claim 1, wherein the method comprises selecting the repetition frequency to control one or more properties of the metal layer.

15. The method according to claim 14, wherein the one or more properties of the metal layer include density, microstructure, conductivity, and/or hardness.

16. The method according to claim 2, wherein the method comprises selecting the repetition frequency to control one or more properties of the metal layer.

17. The method according to claim 16, wherein the one or more properties of the metal layer include density, microstructure, conductivity, and/or hardness.

* * * * *